(12) United States Patent
Lebecque

(10) Patent No.: US 6,338,721 B1
(45) Date of Patent: Jan. 15, 2002

(54) THERAPEUTIC VIBRATOR FOR CORRECTING ERECTILE DYSFUNCTION

(76) Inventor: Maurice Lebecque, 7222 Durocher, π9, Montreal, Quebec (CA), H3N 1Z9

(*) Notice: Subject to any disclaimer, the term of this patent is extended or adjusted under 35 U.S.C. 154(b) by 0 days.

(21) Appl. No.: 09/456,946

(22) Filed: Dec. 7, 1999

Related U.S. Application Data

(60) Provisional application No. 60/111,382, filed on Dec. 9, 1998.

(51) Int. Cl.$^7$ ............................. A61M 11/00; A61F 5/00
(52) U.S. Cl. ............................. 601/71; 601/70; 601/69; 600/38
(58) Field of Search ....................... 600/38, 39; 601/46, 601/67, 69, 70, 71, 78, 79

(56) References Cited

U.S. PATENT DOCUMENTS 5,377,692 A * 1/1995 Pfeil ........................... 128/844
5,397,294 A * 3/1995 Hwang ......................... 601/71

* cited by examiner

Primary Examiner—Jeanette Chapman
Assistant Examiner—Benjamin K. Koo
(74) Attorney, Agent, or Firm—Francois Martineau

(57) ABSTRACT

The vibrator includes a selectively powered vibrating casing, on which an arch is mounted, the combination of the arch with the casing forming a closed loop. A resilient and flexible strap extends through the loop thus created, the strap being bored at its two end portions and being engaged by the two arms of the arcuate arch. The strap is slidable along the two arms of the arch, so that its position be adjustable relative to both the vibrating casing and the upper web of the arch itself.

20 Claims, 10 Drawing Sheets

THERAPEUTIC VIBRATOR FOR CORRECTING ERECTILE DYSFUNCTION

CROSS-REFERENCE DATA

Co-pending provisional patent application No. USA 60/111,382 filed on Dec. 9, 1998, is hereby incorporated by way of reference.

FIELD OF THE INVENTION

The present invention relates to a vibrator, and more particularly to a vibrator for use in correcting erectile dysfunction.

BACKGROUND OF THE INVENTION

It is known to provide already fully-erected penis vibrators for use by men, which include hollow cylindrical casings which are adapted to be engaged by and cover the penis, for frictionally stimulating the outer surface of the penis by reciprocating vibrating motion of the vibrator. However, some problems arise when using such a vibrator:

- the vibrator can only be used by a man, and cannot be used by a woman;
- the vibrator cannot be used if the penis is not in full erection, thus having an erectile dysfunction cannot use the prior art vibrators, as well as those who have an excessively curved penis;
- the vibrator requires manual handling thereof, and thus those suffering from medical conditions resulting in limited manual dexterity often cannot use the vibrator, e.g. those suffering from partial paralysis or psychological traumas;
- the vibrator cannot be used by the man during sexual intercourse; and
- in the case of hollow cylindrical vibrators, they are often not provided with an open outer end, which results in the penis ejaculating inside the vibrator, which requires cleaning of the vibrator and which can bring about hygiene problems.

It is further known to provide small vibrators for women which are destined to be inserted into the woman's vagina. However, these vibrators cannot be used by men.

OBJECTS OF THE INVENTION

It is the gist of the invention to provide a therapeutic device for correcting erectile dysfunction in men, which circumvents the above-noted deficiencies of the prior art penis vibrators.

It is a further object of the present invention to provide such a vibrator which can be used alternately by women.

SUMMARY OF THE INVENTION

The present invention relates to the combination of an arch member for attachment to a selectively powered vibrating casing and a strap member, said arch member comprising a first and a second arms each having a first end portion destined to be attached to the vibrating casing and a second end portion destined to be disposed distally relative to the vibrating casing, said strap member engaging said arch member so as to bridge said first and second arms for defining a passageway between said strap member and the vibrating casing adapted for engagement by a tubular body, said strap member including a releasable fastening device for releasably attaching said strap member at a selected position along said first and second arms, thus selectively adjusting the position of said strap member relative to the vibrating casing.

Preferably, strap member is a flexible resilient strap, and said releasable fastening device is a pair of holes provided in said flexible strap which are respectively engaged by said first and second arms, to allow said strap to be releasably fixed at a selected position along said first and second arms by the frictional engagement of an area of said flexible strap neighbouring said holes against said arch member.

Preferably, said arch member further comprises an arcuate web portion integrally fixed to said second end portion of said first and second arms, thus defining another passageway between said arch member arcuate web portion and said strap adapted for engagement therein of a tubular body, said strap being selectively movable along said arch member first and second arms and said web portion, for selectively adjusting the position of said strap not only relative to the vibrating casing, but also relative to said arch member web portion.

Preferably, said arch member arcuate web portion is releasably attached to said first and second arm members.

Preferably, said first and second arm members are integrally fixed to a foot member for fixed attachment of said foot member to the vibrating casing.

Preferably, said foot member is a bracket for removable attachment thereof to the vibrating casing.

Preferably, said arch member arcuate web portion and first and second arm members have a generally ovoidal cross-section having an inwardly tapering portion.

Preferably, said arch member is provided with a number of spaced notches, an opposite pair of which are engageable by opposite ends of said strap for enhancing the frictional engagement of said strap on said arch member.

Preferably, said arch member arcuate web portion comprises a transverse arcuate marginal edge portion.

Preferably, said resilient strap is made of a flat band of resilient material.

The present invention further relates to a therapeutic device for correcting erectile dysfunction, comprising:

- a vibrating casing;
- a selectively controlled power supply linked to said vibrating casing, for selectively vibrating said casing;
- an arch member attached to said vibrating casing, said arch member comprising a first and a second arms each having a first end portion attached to said vibrating casing and a second end portion disposed distally relative to said vibrating casing; and
- a strap member engaging said arch member so as to bridge said first and second arms wherein a passageway is formed between said strap member and said vibrating casing for frictional engagement therein by a penis, said strap member including a releasable fastening device for releasably attaching said strap member at a selected position along said first and second arms, thus selectively adjusting the position of said strap member relative to said vibrating casing for constant engagement of the penis against the vibrating casing when the penis extends in the passageway.

Preferably, said strap member of said therapeutic deivce is a flexible resilient strap, and said releasable fastening device is a pair of holes provided in said resilient strap which are respectively engaged by said first and second arms, to allow said strap to be releasably fixed at a selected position along said first and second arms by the frictional engagement of an area of said flexible strap neighbouring said holes against said arch member, the resiliency of said strap allowing said strap to yieldingly accomodate the diametral dilatation of the penis when it is inserted in said passageway and it becomes erect.

Preferably, said arch member of said therapeutic device further comprises an arcuate web portion integrally fixed to said second end portion of said first and second arms, thus defining another passageway between said arch member arcuate web portion and said strap for engagement in said another passageway by a penis instead of in said passageway, said strap being selectively movable along said arch member first and second arms and said web portion, for allowing selective adjustment of the position of said strap not only relative to the vibrating casing, but also relative to said arch member web portion for constant engagement of the penis against said arch member when the penis extends in said another passageway, the resiliency of said strap allowing said strap to yieldingly accomodate the diametral dilatation of the penis when it is inserted in said another passageway and it becomes erect.

DETAILED DESCRIPTION OF THE EMBODIMENTS

Figure 1:
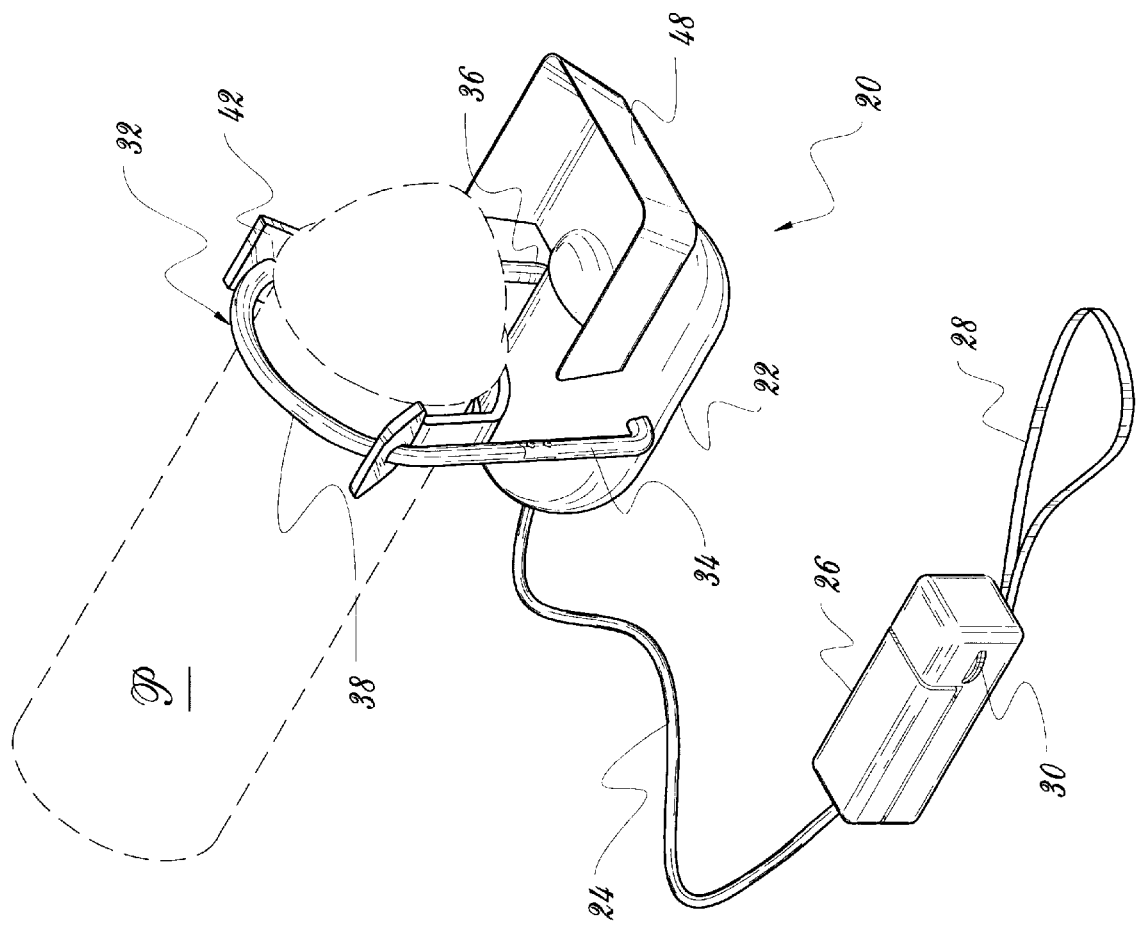
FIG. 1 is a perspective view of the vibrator of the present invention according to a first embodiment, with an erected penis in dotted lines mounted therein, and with the resilient strap being shown in a deformed condition to accomodate the penis.
Figure 2:
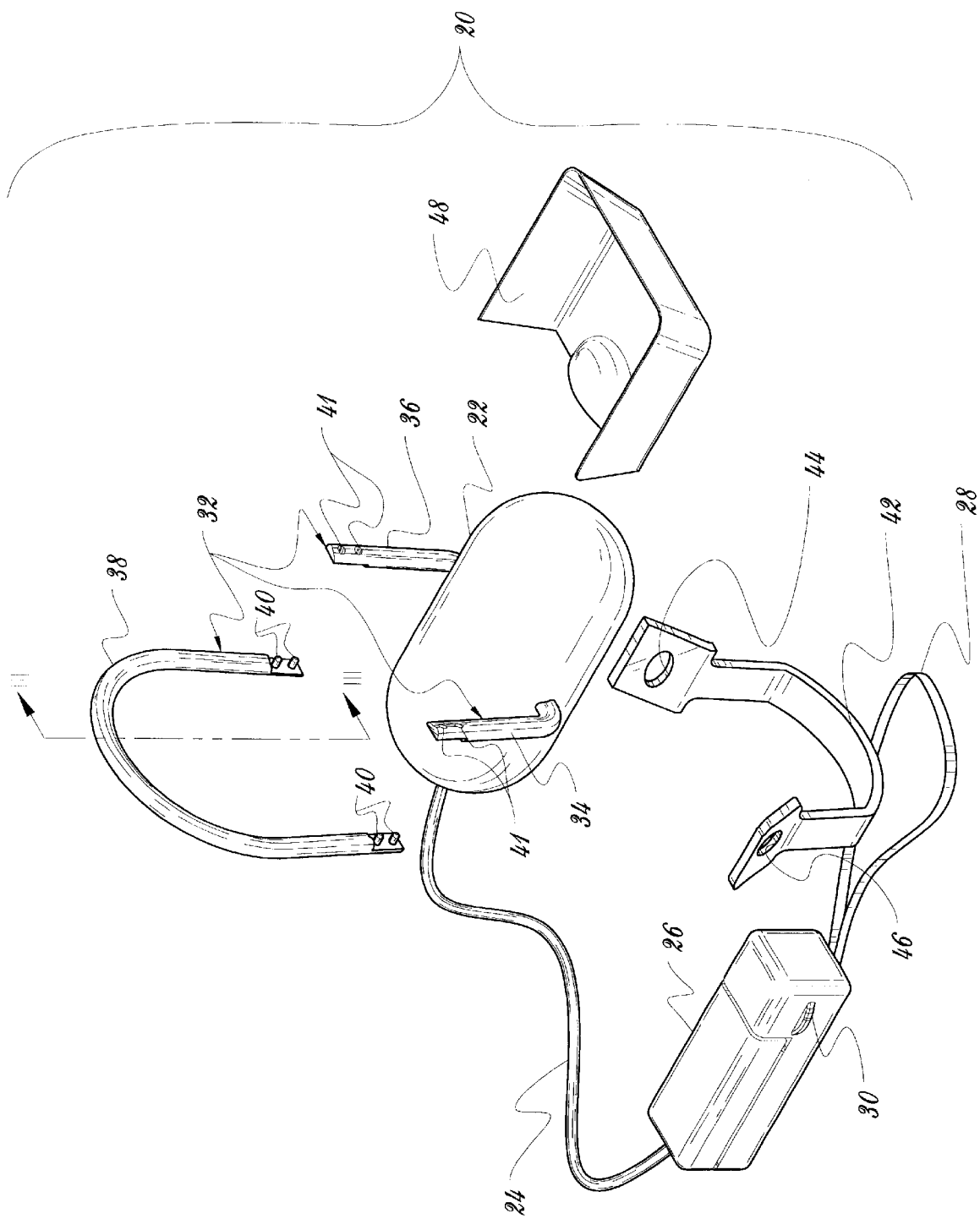
FIG. 2 is an exploded view of the vibrator of FIG. 1.

FIGS. 1 and 2 show a vibrator 20 according to a first embodiment of the invention. Vibrator 20 comprises a vibrating motor (not shown in FIGS. 1 and 2) enclosed in a vibrating casing 22 of known construction, which preferably has a substantially cylindrical outer surface with hemispherical end portions. Casing 22 is linked with a power cord 24 to a power supply casing 26, e.g. holding batteries. A holding strap 28 is provided on power supply casing 26, for holding or hanging casing 26 in a desired fashion. Power supply casing 26 is further provided with a control button 30 which allows selective activation and intensity control over the vibrations of vibrating casing 22.

Figure 3:
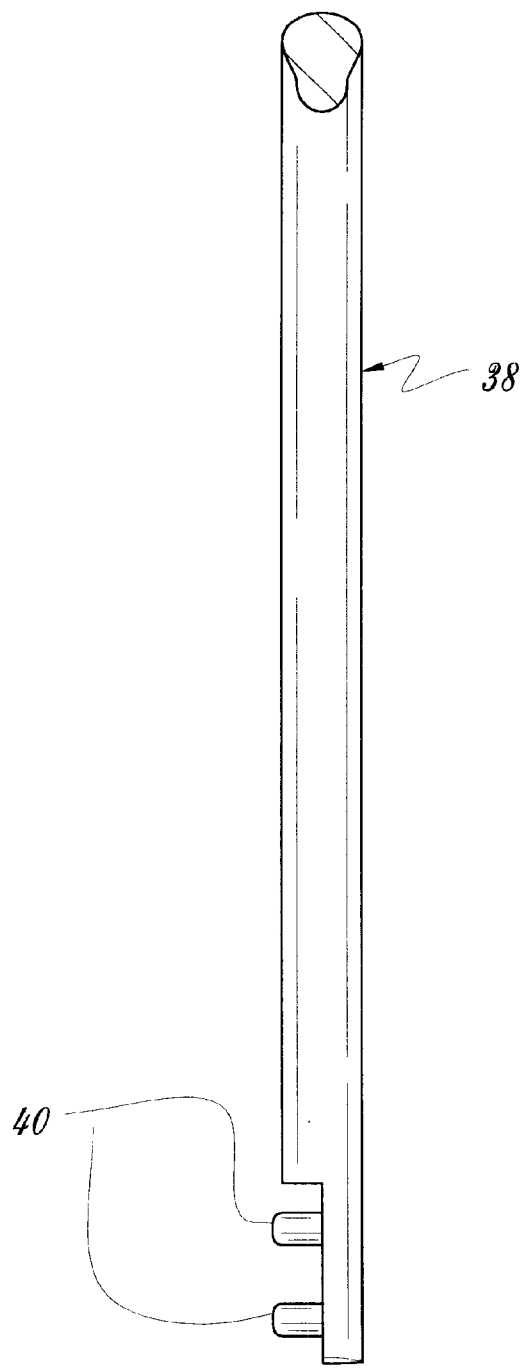
FIG. 3 is an enlarged cross-sectional view of the arch of the vibrator, taken along line III—III of FIG. 2.

Vibrator 20 further comprises, according to the present invention, a rigid arch member 32 sized for engagement therein of an erected penis. Arch member 32 includes a pair of support arms 34, 36 integrally fixed (e.g. glued) to opposite sides of the intermediate cylindrical portion of casing 22, and an arcuate web portion 38 which engages in a coextensive fashion, by means of short transverse studs 40 provided at its two extremities, the upper extremities of the support arms 34, 36 which are complementarily bored at 41 to receive studs 40 in a snap-fit type engagement. Glue can further be used to permanently fasten arcuate web portion 38 to support arms 34, 36. As shown in FIG. 3, web portion 38 has an ovoidal inwardly tapering cross-section, the smaller inner radius of curvature helping to prevent accidental sliding of the web portion 38 on the penis.

Figure 4:
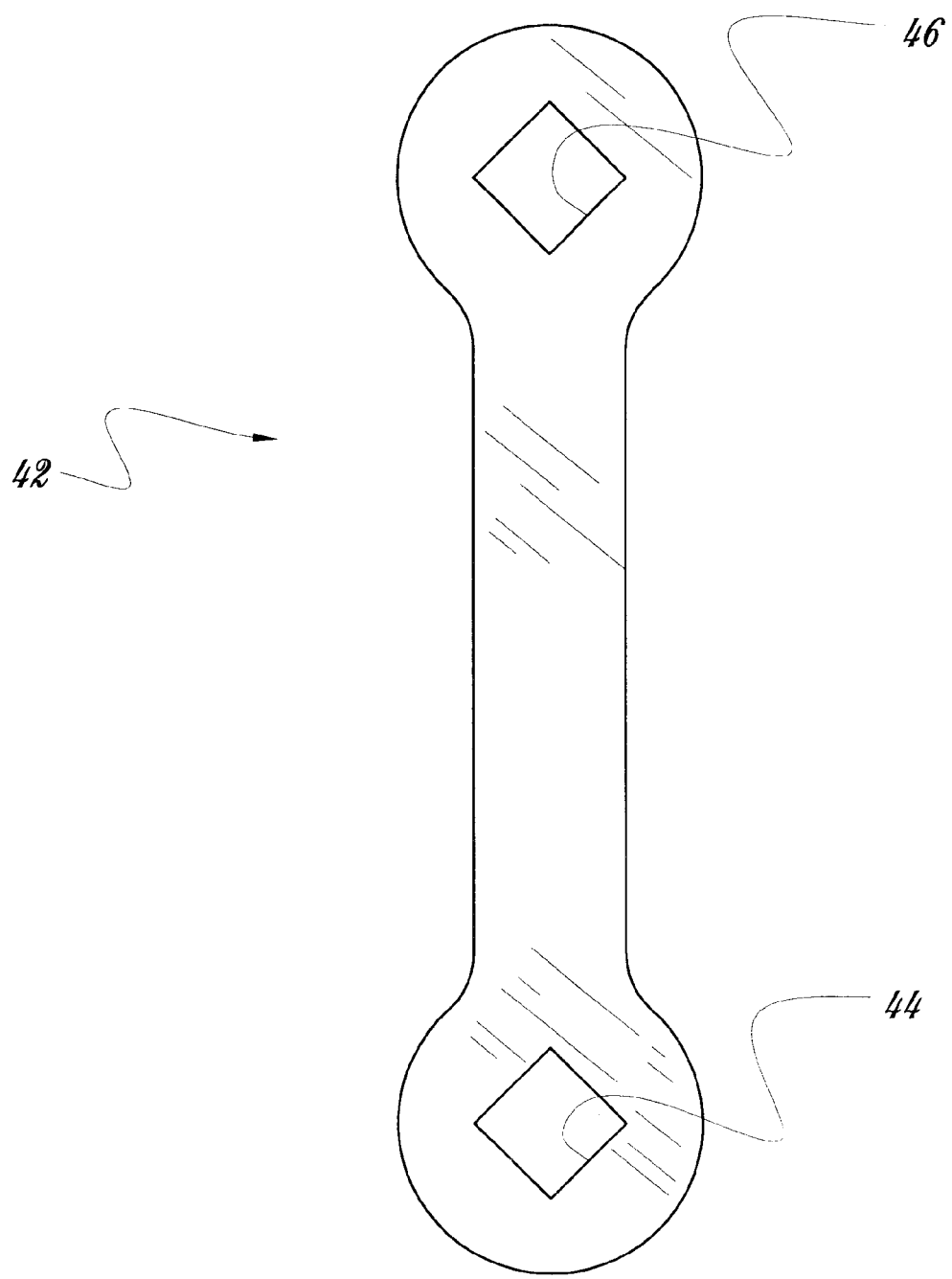
FIG. 4 is an enlarged top plan view of the flexible strap of the vibrator of FIGS. 1–2.

Vibrator 20 further comprises a flexible and resilient flat strap 42 which is bored at its two outer end portions at 44, 46. Bores 44, 46 engage arms 34, 36 so as to be slidable on opposite sides of vibrator 20 along arms 44, 46 and the coextensive web portion 38. Preferably, as shown in FIGS. 2 and 4 respectively, strap 42 has either circular or square-shaped openings 44, 46.

An ejaculate fluid receptacle 48 can be installed at the front end portion of the vibrating casing, being glued thereon. Disposable paper or plastic cups (not shown) can be installed therein, for use in sperm collection clinics.

In use, as suggested in FIG. 1, the free end portion of man's penis P is inserted through arch member 32, with strap 42 being afterwards upwardly pulled against the penis underside and lateral sides. Penis P may be fully erected, partly so or not at all. As shown in FIG. 1, arms 34, 36 and web portion 38 have a same size and shape, to prevent the sliding motion of the strap 42 between web portion 38 and arms 44, 46 to be hindered by any protruding edges while strap 42 is being pulled against the penis underside. Once strap 42 is installed against the penis P as shown in FIG. 1, the friction of the area of strap 42 neighbouring holes 44, 46 on arch member 32 prevents ulterior accidental sliding motion of strap 42. The resiliency of strap 42 allows it to yieldingly deform under the presence of penis P, to conform itself to the shape of the penis underside. When no penis P is inserted through the arch member, strap 42 remains straight.

When the power supply 26 is activated, the vibrating casing 22 vibrates and the vibrations are transmitted through rigid arch member 32 to the penis, hence provoking an erection if there is none, and/or stimulating the penis. The resilient strap 42 will resiliently yield to accommodate the increasing diameter of the penis P while maintaining constant contact therewith during progression of erectile dilatation of the penis. Strap 42 allows the penis to be applied against arch member 32 at all times, and simultaneously stimulates the penis underside. Strap 42 accommodates penises of varying sizes and shapes, including a penis that is not erect. Alternately, the penis underside can rest directly on the vibrating casing in arch member 32 and under strap 42, and strap 42 can be downwardly pulled on the upper surface and lateral sides of the penis (this alternate position is not shown in the drawings).

Figure 5:
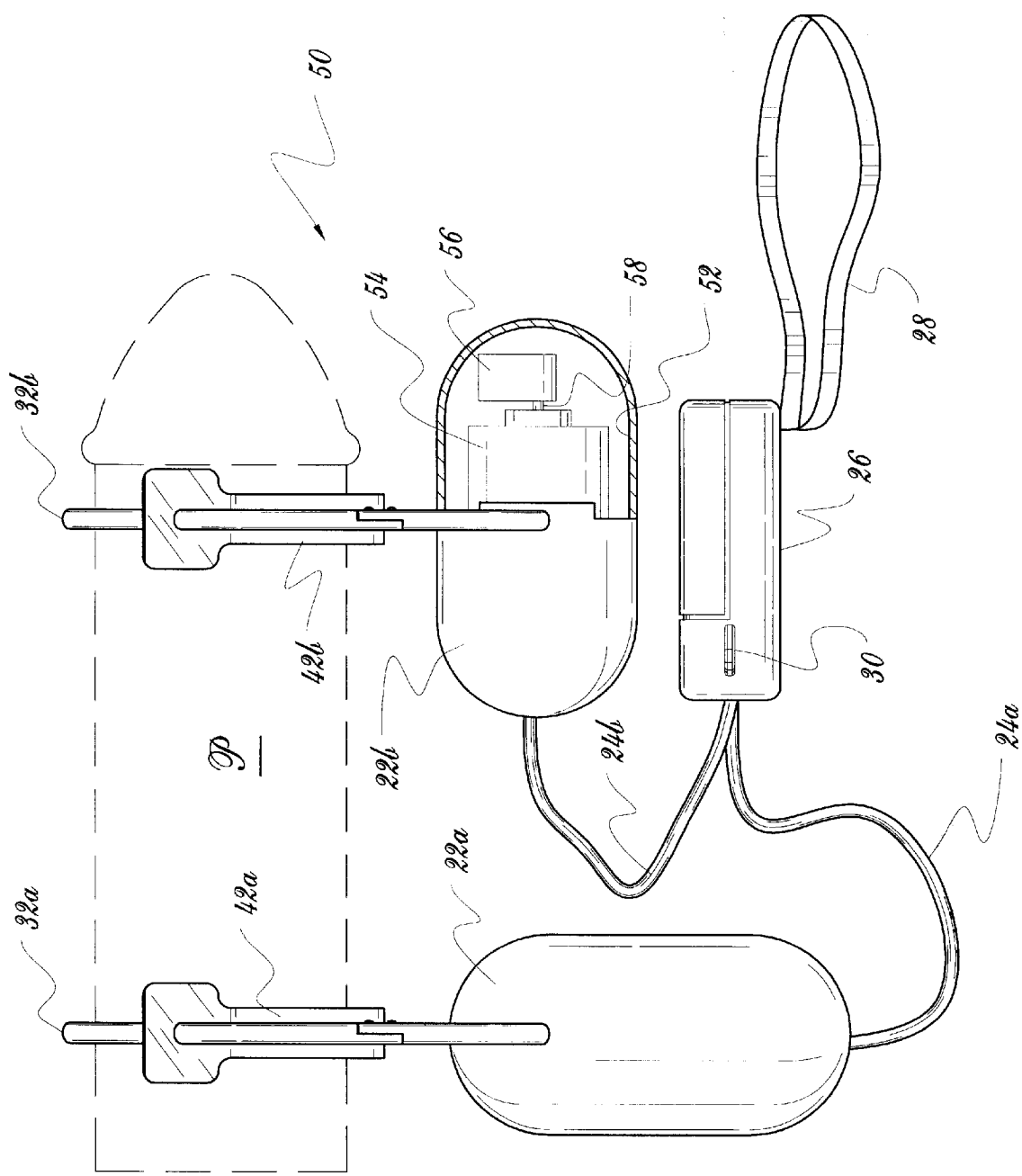
FIG. 5 is a partly sectional side elevation of a second embodiment of a vibrator according to the invention, with an erected penis in dotted lines mounted therein in operative position, and with the resilient strap being shown in a deformed condition.

FIG. 5 shows a second embodiment of a vibrator 50 according to the invention, which is similar to the first embodiment, except as noted hereinafter. In this second embodiment, vibrator 50 includes a pair of axially spaced, relative to penis P, vibrating casings 22a, 22b linked to a power supply casing 26 by first and second power supply wires 24a, 24b. Vibrating casings 22a, 22b are each provided with arch members 32a, 32b and resilient straps 42a, 42b. Casing 22a is shown to support its arch member 32a in a coextensive manner instead of a transverse manner: this is an alternate way of assembling these elements, but otherwise the vibrating casing 22a and arch member 32a assembly are similar to the one of the first embodiment.

FIG. 5 shows that vibrating casing 22b includes a hollow inner chamber 52 in which a motor 54 is installed, with a rotating weight 56 being fixedly and eccentrically attached at the outer end of the motor's rotating output shaft 58. As stated hereinabove, this vibrating casing is of known construction. Casings 22a and 22 are similarly equipped.

The embodiment shown in FIG. 5 thus includes a pair of vibrating casings 22a, 22b each provided with an arch member 32a, 32b and a strap 42a, 42b for stimulating the man's penis in two different areas, namely the opposite end portions of the penis. It is understood that a single one of the casing-arch member-strap assemblies 22a, 32a, 42a and 22b, 32b, 42b could be used, in combination with a power supply casing 26; and that each assembly 22a, 32a, 42a and 22b, 32b, 42b could also be provided with its individual power supply.

Furthermore, it can be seen that when a vibrator arch member 32a and vibrating casing 22a are located near the root of the penis (without any other arch member 32b or casing 22b), the short length of the penis occupied by arch member 32a allows most of the remaining frontward portion of the penis to be free for sexual intercourse with a partner. In such a case, the vertically aligned casing 22a and arch member 32 disposition is especially desirable, since it becomes less cumbersome.

Figure 6:
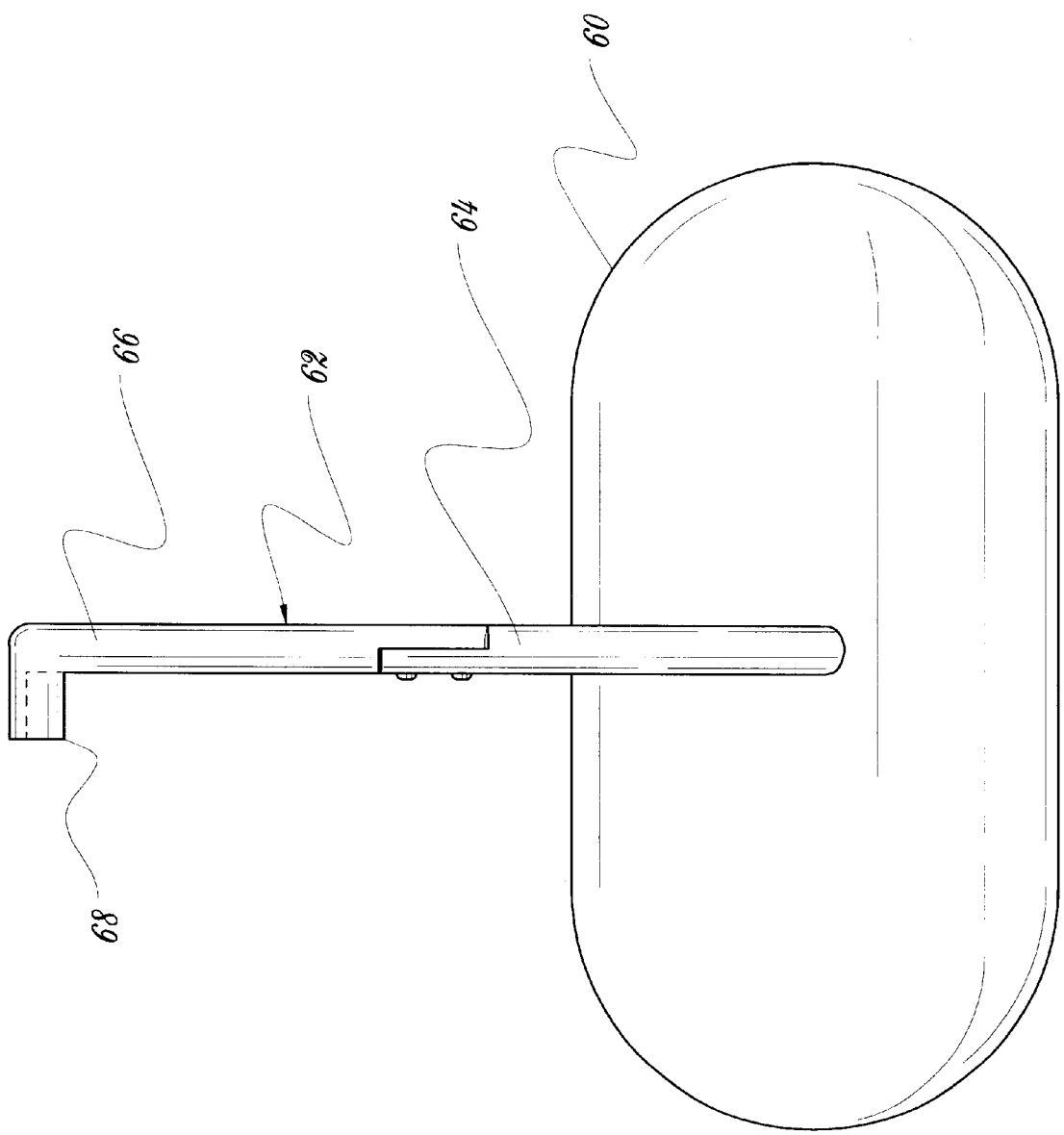
FIG. 6 is a side elevation at an enlarged scale of a third embodiment of a vibrator according to the invention.

FIG. 6 shows a third embodiment of a vibrator according to the invention, which includes a vibrating casing 60 destined to be connected to a power supply casing (not shown in FIG. 6) as shown in the first and second embodiments of the invention. Casing 60 supports an arch member 62 having a first and a second support arms 64 (with one support arm being concealed in FIG. 6) carrying an arcuate web portion 66 having a transversely extending arcuate upper marginal edge portion 68 which is destined to extend in use onto the upper portion of the glans of the penis, for enhancing the stimulating effect of the vibrator.

Figure 7:
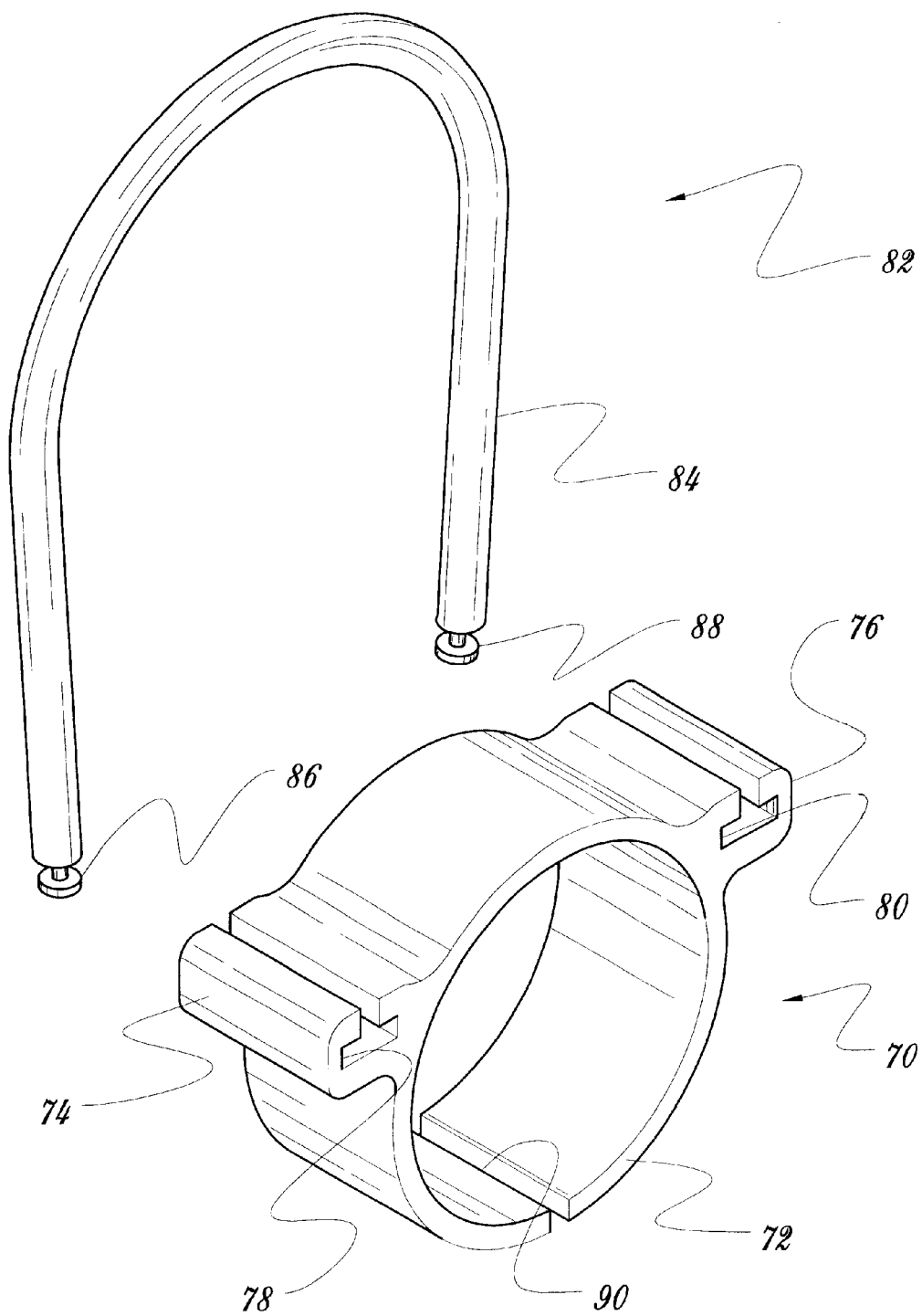
FIG. 7 is an exploded perspective view of an alternate embodiment of an arch and a bracket for use with a vibrator according to the invention.

FIG. 7 shows an alternate embodiment of an arch member for use with a vibrating casing such as casing 22 shown in FIGS. 1 and 2. More particularly, FIG. 7 shows a bracket 70 which has a hollow cylindrical main body 72 supporting laterally projecting support arms or wings 74, 76 which have coplanar elongated parallel T-shaped slots 78, 80. An arch 82 is formed by an arcuate main body 84 having two lower end portions provided with pins 86, 88 coextensive with the arch 84 lower end portions, pins 86, 88 being sized and shaped to slidingly fit into slots 78, 80. Preferably, a friction-fit engagement will occur, although a snap-fit or glue or other suitable fastening means are also envisioned to secure pins 86, 88 in slots 78, 80.

The bracket 70 of the embodiment of FIG. 7 is destined to fit onto the cylindrical body of a vibrating casing such as casing 22 shown in FIGS. 1 and 2 for use by a man. As shown in FIG. 7, the bracket main body preferably has a longitudinal slit 90 to allow resilient yielding deformation thereof, the bracket 70 then tightly resiliently fitting onto the vibrating casing outer cylindrical surface. Thus, the vibrating casing can alternately be used by a woman, by removing bracket 70 from the vibrating casing of the vibrator, for allowing the casing to be used by a woman, for insertion into a woman's vagina. Also, arch 82 can be removed from bracket 70, to install an arch of different configuration, such as arch 92 shown in FIG. 8.

Figure 8:
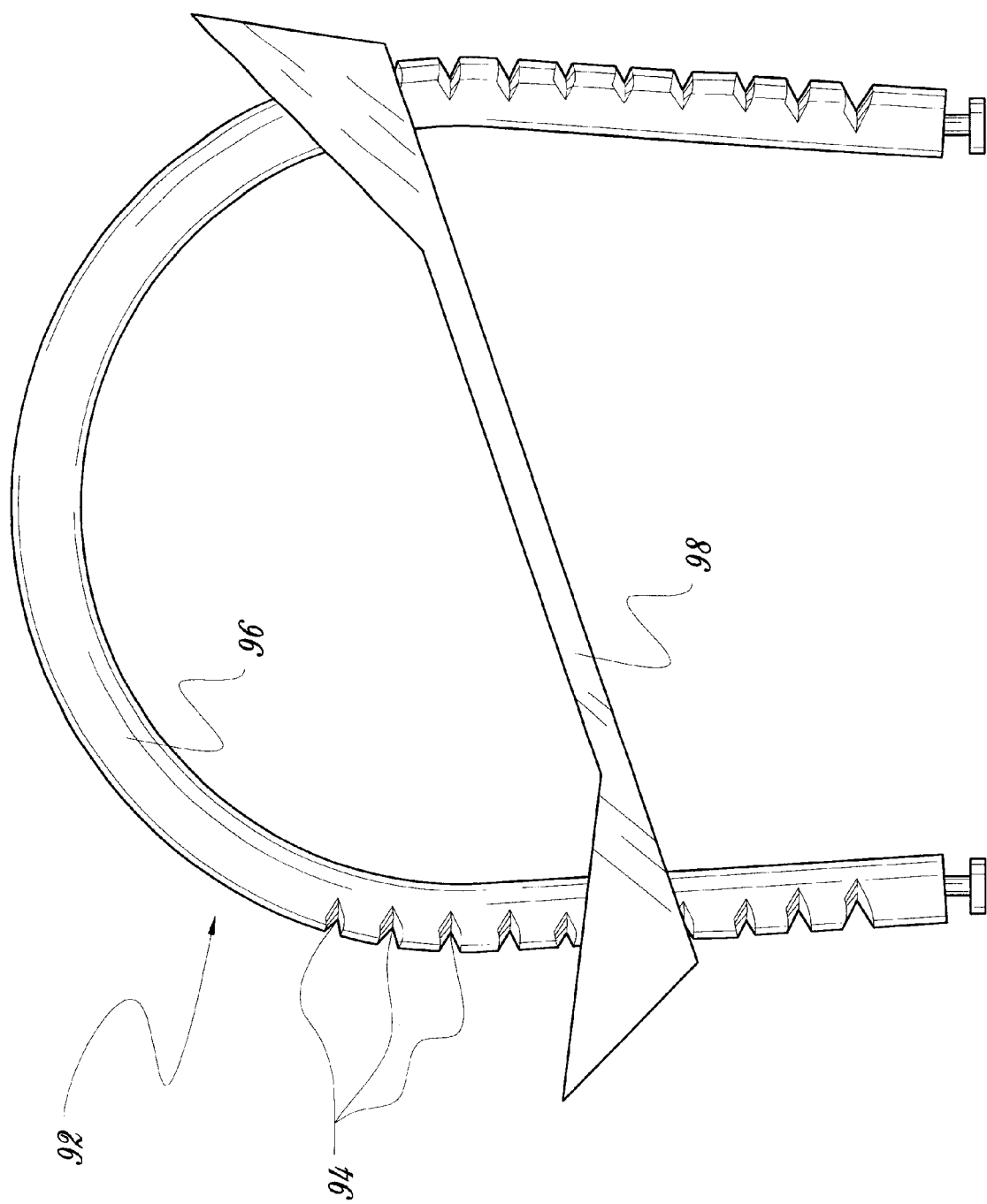
FIG. 8 is a front elevation of another alternate embodiment of an arch for use with a vibrator according to the invention.

The arch 92 of FIG. 8 is similar to that of FIG. 7, except that it is moreover provided with a plurality of notches 94 on the outer surface of each of the two legs of its main body 96. Notches 94 allow the resilient strap 98, similar to strap 42 shown in FIG. 4, to be installed in an asymmetrical fashion on arch member 92, without sliding back into a symmetrical position. The purpose of this embodiment is to allow use of the vibrator according to the invention by men having a penis of an unconventional shape.

Figures 9, 10:
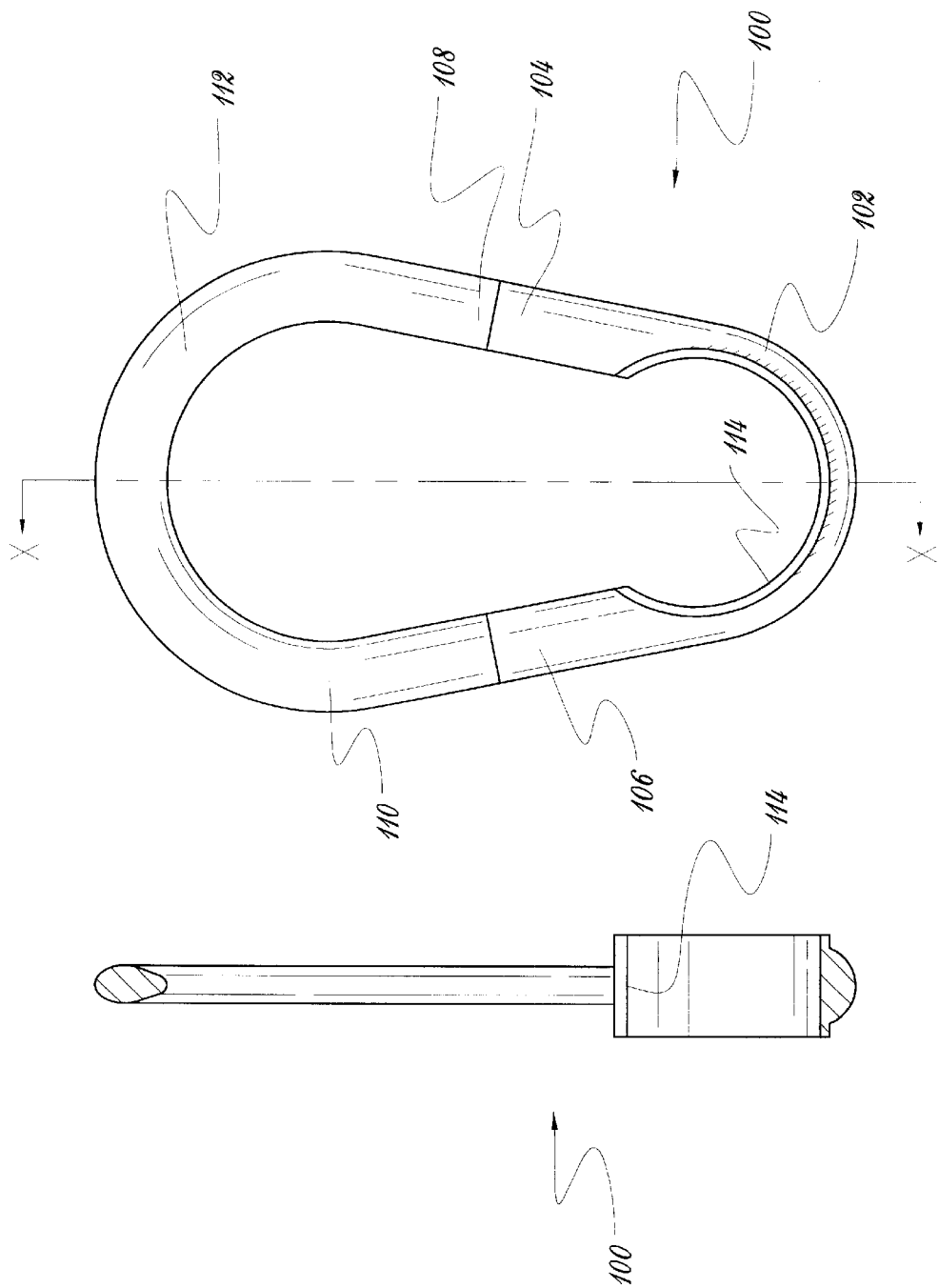
FIG. 9 is a front elevation of yet another alternate embodiment of an arch for use with a vibrator according to the present invention.
FIG. 10 is a cross-sectional view taken along line X—X of FIG. 9.

FIGS. 9 and 10 show yet another embodiment of an arch member 100 which is similar to the arch members of the previous embodiments, except as noted hereinafter. Arch member 100 comprises a foot member 102 which is horseshoe-shaped, and two upwardly extending arms 104, 106 which are integrally formed with and coextensive to the upper end portions of foot member 102, arms 104, 106 being engaged by and fixedly attached to corresponding extremities 108, 110 of the arcuate web 112 of arch member 100. Thus, arch member 100 forms an integral closed loop. Foot member has an inner flange 114 of wider configuration and having a truncated cylindrical shape, flange 114 being sized to fit onto the outer cylindrical surface of a vibrating casing such as casing 22 of FIGS. 1 and 2. Preferably, flange 114 is glued onto such a vibrating casing, although alternate attachments allowing the arch member 100 to be removed are also envisioned. The advantage of the embodiment of the arch member 100 shown in FIGS. 9 and 10 is that it may be sold in combination with the known vibrating casing and power supply, for easy installation of arch member 100 onto the vibrating casing by the end user himself instead of during production.

Figure 11:
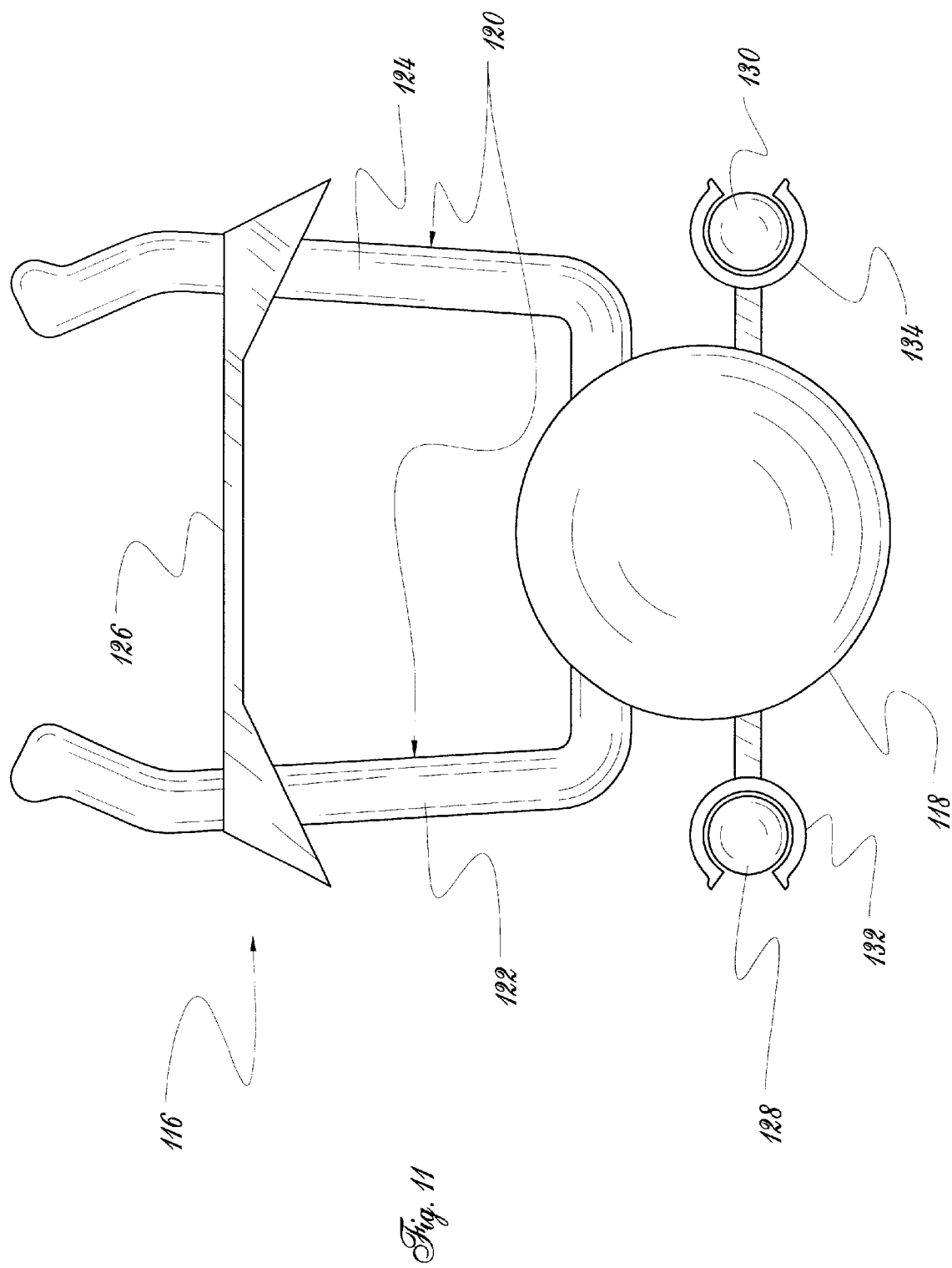
FIG. 11 is a front elevation of a fourth embodiment of a vibrator according to the invention.

FIG. 11 shows yet another embodiment of a vibrator 116 according to the present invention. In this embodiment, the vibrating casing 118, connected to a power supply (not shown in FIG. 11), supports an arch member 120 formed of a first and a second distinct arms 122, 124 which are generally parallel to each other, except for short elbowed portions at their lower ends which converge towards the casing 118 for attachment thereto. A resilient strap 126, similar to strap 42 shown in FIG. 4, is installed on arms 122, 124. In this embodiment, the penis of the man can only be inserted between strap 126 and vibrating casing 118. The upper portions of arms 122, 124 are not linked to each other by an arch member web portion as with the previous embodiments.

In the embodiment of FIG. 11, it is shown that casing 118 further supports two metallic rods 128, 130 by means of side brackets 132, 134 attached on one side and the other of casing 118. Rods 128, 130 are removable, and act as so-called dead weights, to add weight to vibrator 116, for those who prefer a heavier vibrator. Also, the vibrating frequency will be modified by weights 128, 130, thus providing a different feeling.

It is understood that any modifications to the present invention, which do not deviate from the scope thereof, are considered to be included therein.

For example, different alternate embodiments each including several features have been disclosed in the present specification. It must be understood that a number of these features could be selectively combined or left out when the vibrator is produced. For example, the dead weights 128, 130 shown in the embodiment of FIG. 11 could be installed on any and all of the previous embodiments. Other such optional features include non-exclusively: the bracket allowing for a removable arch member, the notches for allowing the flexible strap to be tensioned asymmetrically between the opposite sides of the arch member, the upper marginal edge portion of the arch member for enhancing the stimulating effect on the penis glans, the use of a second vibrating casing and arch assembly, and the sperm receptacle. Also, it is understood that any of the different methods of attaching the arch member to the vibrating casing described in the present specification, as well as any further method which would be obvious for someone skilled in the art of the invention, could be used in combination with a number of the above-described optional features.

Also, although the strap is preferably resilient, it is envisioned that it be non-resilient, either flexible and even rigid, if an alternate releasable fastening device is provided for selectively fastening the strap at a selected position along the arch member. This non-resilient strap member is not the preferred way to carry out the invention however, since it will not be able to so easily accomodate the penis erectile dilatation progressive increase of size while circumscribing the penis underside and lateral sides in a suitable manner for all penis diameters.

Throughout the present specification, the expression "arch member" has been used to characterize the element holding the flexible strap. This element, as shown in the embodiment of FIG. 11, can take the form of a pair of distinct arms, with the strap bridging these arms and thus forming an arch. It must thus be understood that the expression "arch member" is not limited to a rigid arcuate monolithic rod, but must be taken in the general sense of the element which supports the flexible strap or strap member. In the end, an arch will be formed over the vibrating casing to circumscribe the penis, be it by an arcuate web portion of the arch member, or by the overlying strap bridging the arms forming the arch member.

I claim:

1. In combination, an arch member for attachment to a selectively powered vibrating casing, said arch member comprising a first and a second elongated arms each having a first end portion destined to be attached to the vibrating casing and a second end portion destined to be disposed distally relative to the vibraing casing; and an elongated strap member defining a first end portion engaging said arch member first arm and a second end portion engaging said arch member second arm so as to bridge said first and second arms for defining a first passageway between said strap member and the vibrating casing adapted for engagement by a tubular body, said strap member first and second end portions including positional adjusLtment means positioning said strap member first and second end portions at selected positions along said first and second arms respectively, for selectively adjusting the position of said strap member relative to the vibrating casing and consequently for varying the size of said first passageway.

2. The combination as defined in claim 1, wherein said strap member is a flexible and resilient flat band and includes a pair of holes respectively provided at said first and second end portions of said strap member and which are respectively engaged by said first and second arms, said positional adjustment means including said holes that allow said strap member first and second end portions to be releasably fixed at a selected position along said first and second arms by the frictional engagement of an area of said flexible strap member neighbouring said holes against said arch member.

3. The combination as defined in claim 2, wherein said arch member further comprises an arcuate web portion integrally fixed to said second end portion of said first and second arms and destined to be in spaced-apart facing register with said casing, said arcuate web portion, said first arm, said second arm and said strap member defining a second passageway distinct of said first passageway adapted for engagement therein of a tubular body, and wherein said positional adjustment means allow said strap member to be selectively positioned relative to said arch member web portion and consequently to selectively vary the size of said second passageway.

4. The combination as defined in claim 3, wherein said arch member arcuate web portion is releasably attached to said first and second arm members.

5. The combination as defined in claim 3, wherein said first and second arm members are integrally fixed to a foot member for fixed attachment of said foot member to the vibrating casing.

6. The combination as defined in claim 5, wherein said foot member is a bracket for removable attachment thereof to the vibrating casing.

7. The combination as defined in claim 3, wherein said arch member arcuate web portion and first and second arm members have a generally ovoidal cross-section having an inwardly tapering portion.

8. The combination as defined in claim 3, wherein said arch member is provided with at least two spaced notches on each said first and second arms, an opposite pair of which are engageable by opposite ends of said strap for enhancing the frictional engagement of siad strap on said arch member.

9. The combination as defined in claim 3, wherein said arch member arcuate web portion comprises a transverse arcuate marginal edge portion.

10. A therapeutic device for correcting sexual dysfunction, comprising:
   a vibrating casing;
   a selectively controlled power supply linked to said vibrating casing, for selectively vibrating said casing;
   an arch member attached to said vibrating casing, said arch member comprising a first and a second elongated arms each having a first end portion attached to the vibrating casing and a second end portion disposed distally relative to said vibrating casing; and
   an elongated strap member defining a first end portion engaging said arch member first arm and a second end portion engaging said arch member second arm so as to bridge said first and second arms wherein u first passageway is formed between said strap member and said vibrating casing for frictional engagement therein by a penis, said strap member first and second end portions including positional adjustmcnt means positioning said strap member first and second end portions at selected positions along said first and second arms respectively, thus selectively adjusting the position of said Strap member relative to said vibrating casing and consequently varying the size of said first passageway for constant engagement of the penis against the vibrating casing when the penis extends said first passageway.

11. A therapeutic device as defined in claim 10, wherein said strap member is a flexible and resilient flat band and includes a pair of holes respectively provided at said first and second end portions of said strap member and which are respectively engaged by said first and second arms, said positional adjustment means including said holes that allow said strap member first and second end portions to be releasably fixed at a selected position along said first and second arms by the frictional engagement of an area of said flexible strap member neighbouring said holes against said arch member, the resiliency of said strap allowing said strap to yieldingly accommodate the diarmetral dilatation of the penis when it is inserted in said first passageway and it becomes erect.

12. A therapeutic device as defined in claim 10, further including an ejaculate fluid receptacle mounted to said vibrating casing.

13. A therapeutic device as defined in claim 11, wherein said arch member further comprises an arcuate web portion integrally fixed to said second end portion of said first and second arms and destined to be in spaced-apart facing register with said casing, said arcuate web portion, said first arm, said second arm and said strap member defining a second passageway distinct of said first passageway adapted for engagement in said second passageway by a penis instead of in said first passageway, and wherein said positional adjustment means allow said strap member to be selectively positioned relative to said arch member web portion for constant engagement of the penis against said arch member when the penis extends in said second passageway and consequently to selectively vary the size of said second passageway, the resiliency of said strap member together with the adjustable position of said strap member allowing said strap member to yieldingly accommodate the diametral dilatation of the penis when it is inserted in said second passageway and it becomes erect.

14. A therapeutic device as defined in claim 13, wherein said arch member arcuate web portion is releasably attached to said first and second arm members.

15. A therapeutic device as defined in claim 13, wherein said first and second arm members are integrally fixed to a foot member for fixed attachment of said foot member to the vibrating casing.

16. A therapeutic device as defined in claim 15, wherein said foot member is a bracket for removable attachment thereof to the vibrating casing.

17. A therapeutic device as defined in claim 13, wherein said arch member arcuate web portion and first and second arm members have a generally ovoidal cross-section having an inwardly tapering portion.

18. A therapeutic device as defined in claim 13, wherein said arch member is provided with at least two spaced notches on each said first and second arms, an opposite pair of which are engageable by opposite ends of said strap for enhancing the frictional engagement of said strap on said arch member.

19. A therapeutic device as defined in claim 13, wherein said arch member arcuate web portion comprises a transverse arcuate marginal edge portion.

20. A therapeutic device for correcting sexual dysfunction, comprising:

a selectively powered vibrating casing;

an arch member attached to said vibrating casing and comprising a web portion and a first and a second elongated arms each having a first end portion destined to be attached to the vibrating casing and a second end portion destined to be disposed distally relative to the vibrating casing, said web portion being in spaced-apart facing register with said casing; and an elongated resilient strap member defining a first end portion engaging said arch member first arm and a second end portion engaging said arch member second arm so as to bridge said first and second arms for defining a passageway between said strap member, said first arm, said second arm and said web portion for engagement therein by a penis, said strap member first and second end portions including a relcasable fastening device that position said strap member first and second end portions at sclected positions along said first and second arms respectively, to selectively adjust the position of said strap member relative to said web portion and to consequently vary the size of said passageway to accommodate penises of varying sizes notwithstanding any resilient yielding deformation of said resilient strap member.

* * * * *

UNITED STATES PATENT AND TRADEMARK OFFICE
CERTIFICATE OF CORRECTION

PATENT NO. : 6,338,721 B1
DATED : January 15, 2002
INVENTOR(S) : Maurice Lebecque It is certified that error appears in the above-identified patent and that said Letters Patent is hereby corrected as shown below:

Column 7,
Line 45, "vibraing" should read -- vibrating --;
Line 52, "adjusLtment" should read -- adjustment --;

Column 8,
Line 31, "siad" should read -- said --;
Line 48, "u" should read -- a --;
Line 52, "adjustcnt" should read -- adjustment --;
Line 55, "Strap" should read -- strap --;

Column 9,
Line 4, "diarmetral" should read -- diametral --;

Column 10,
Line 30, "rclcasable" should read -- releasable --;
Line 32, "sclected" should read -- selected --.

Signed and Sealed this

Fourteenth Day of January, 2003

JAMES E. ROGAN
*Director of the United States Patent and Trademark Office*